United States Patent [19]
Zamba et al.

[11] Patent Number: 4,955,371
[45] Date of Patent: Sep. 11, 1990

[54] DISPOSABLE INHALATION ACTIVATED, AEROSOL DEVICE FOR PULMONARY MEDICINE

[75] Inventors: Gene Zamba, Brooklyn, Conn.; Stephen C. Glazier, New York, N.Y.

[73] Assignee: Transtech Scientific, Inc., New York, N.Y.

[21] Appl. No.: 348,424

[22] Filed: May 8, 1989

[51] Int. Cl.$^5$ .............................................. A61M 16/00
[52] U.S. Cl. ........................... 128/200.18; 128/200.21; 128/200.23; 239/461
[58] Field of Search ....................... 128/200.14, 200.15, 128/200.18, 200.21, 200.22, 200.23, 204.25, 207.12, 205.24; 239/461, 471, 473, 487

[56] References Cited

U.S. PATENT DOCUMENTS

| | | | |
|---|---|---|---|
| 3,605,738 | 9/1971 | Ciranna | 128/200.23 |
| 3,915,164 | 10/1975 | Bird | 128/200.14 |
| 4,470,412 | 9/1984 | Nowacki et al. | 128/200.18 |
| 4,471,773 | 9/1984 | Bunnell et al. | 128/200.21 |
| 4,512,341 | 4/1985 | Lester | 128/200.21 |
| 4,592,349 | 6/1986 | Bird | 128/204.24 |
| 4,796,614 | 1/1989 | Nowacki et al. | 128/200.14 |
| 4,803,978 | 2/1989 | Johnson et al. | 128/200.23 |
| 4,834,083 | 5/1989 | Byram et al. | 128/200.23 |

FOREIGN PATENT DOCUMENTS

| | | | |
|---|---|---|---|
| 483193 | 2/1976 | Australia | 428/200.21 |
| 0014814 | 9/1980 | European Pat. Off. | 128/200.23 |
| 0045419 | 2/1982 | European Pat. Off. | 128/200.23 |
| 281650 | 7/1987 | European Pat. Off. | 128/200.14 |
| 861999 | 3/1961 | United Kingdom | 128/200.21 |

Primary Examiner—Eugene H. Eickholt
Attorney, Agent, or Firm—Harrison & Egbert

[57] ABSTRACT

A disposable device for dispensing an aerosol spray medicament to the lungs of a patient from a stanardized aerosol dispenser activated automatically by the inhaling of the user. The device has only one moving part, and no power requirements. The device may be used alone or within a respirator, by asthmatics, pulmonary cancer patients, and others. The device comprises a body having an outwardly extending nozzle, a receptacle formed within the body for receiving the dispenser, and an activator positioned within the body being mechanically interactive with the inhalation by the patient. Vents are formed in the body for carbureting air into the nozzle. A fixator is provided for detachably affixing the dispenser in position within the receptacle. Specifically, the fixator is a cap that is threadedly connected to the body and has an interior area suitable for accommodating the dispenser. The activator comprises a diaphragm positioned within the body. The diaphragm has an elastic quality suitable for being deformable upon a reduction or increase of air pressure within the nozzle. The activator further includes a pin that is fixedly positioned to the diaphragm and extends upwardly transverse to the plane of the diaphragm. The pin acts as a valve between the dispenser and the nozzle. An atomizer is provided between the receptacle and the nozzle for transmitting fluid into the nozzle. A timer may be attached to the device to provide periodic doses when used with an automatic respirator.

21 Claims, 7 Drawing Sheets

DISPOSABLE INHALATION ACTIVATED, AEROSOL DEVICE FOR PULMONARY MEDICINE

TECHNICAL FIELD

The present invention relates to inhalation devices. Specifically, the present invention relates to inhalation devices capable of dispensing an aerosol medication by way of a breath activated mechanism.

BACKGROUND ART

There are a variety of inhalation devices which release aerosol medication, in a continuous spray or in a metered dose or predetermined amount of medication, directly into the patient's mouth. Typically, these devices were activated by the pressured actuation of the user's fingers, button action, or other related manual techniques, although some are activated by the inhaling action of the user. Heretofore, no simple cheap disposable reliable breath activated devices were developed, and consequently no breath activated devices have reached the market.

Measured dose aerosol canisters of the medicine to be inhaled into the lungs are manufactured in standard sizes by a variety of pharmaceutical companies. These aerosols are much the same as normal aerosol cans, except that when the nozzle pin is depressed, continuous spray does not result; instead a short spray releases a fixed amount of medicine. The spray stops until the nozzle pin is released and depressed again. Currently, these aerosols are used with manually activated inhaler devices that mix atmospheric air with the sprayed medication, permitting a complete breath of air by the patient with his medicine. Aerosol medicines are also available in continuous spray aerosols which continually spray as long as the nozzle pin is depressed.

Proper use of these manual activated devices requires that the spray be activated at the beginning of the breath, so that all the medicine is carried to the lungs as required, and not left in part in the mouth, throat, or spray device, where it is useless. If not all the medicine reaches the lungs, then it is difficult to determine the size of pulmonary dose actually received, and how big a "make up" dose is needed. Over-dosage can be as big a problem as under-dosage. Hence, the timing of the spray activation is critical to proper medication.

Inhalation drug delivery to the lungs is commonly used by asthmatics. Asthma tends to strike small children and old people. These age groups often have bad coordination and weak hands, which can be worsened by the onset of the asthma attack. Hence, the timing of the breadth spray of medicine can be a difficult problem for the people who need it. Heretofore, there has been a frustrated need for a simple disposable device that automatically activates the specific dose medicine spray canisters at the very start of the inhalation on the device.

The prior art teaches a variety of devices to administer medicine to the lungs by spraying while inhaling, but they are manually activated and not activated by the inhalation activity. As a result, these devices do not solve or address the timing or coordination problem with such sprays.

U.S. Pat. No. 3,776,227, issued to Pitesky, et al, on Dec. 4, 1973, discloses a device whereby a cartridge containing gas under pressure is opened by a pin which results in a flow of released gas. The opening is activated by manually rotating a housing containing a pressurized container and valve-supported head relative to one another until the cartridge is punctured U.S. Pat. No. 3,326,231, issued to Hogg, on June 20, 1967, discloses a fluid regulating valve mechanism whereby the flow rate of a fluid released from a puncturable storage container which is ultimately inhaled by the user is metered by regulating the size of the needle valve formed when the pin pierces the container. This process is started by manually depressing an actuator so that the pin will pierce into the compressed container. U.S. Pat. No. 3,045,671, issued to Updegraff, on July 24, 1962, discloses a device whereby a cartridge containing gas under pressure is pierced by a hollow pin or needle which releases a gas which is ultimately inhaled by the user. The piercing of the pressured capsule containing the gas is performed by manually screwing the pin into the cartridge as sealed. U.S. Pat. No. 3,012,694, issued to Johnston, on Dec. 12, 1961, discloses a gas dispensing device whereby gas contained in a pressurized container is released when a point punctures the container. A hand wheel manually operates a threaded member which moves the capsule closer to the point which eventually punctures the container. A sleeve may manually be moved to restrict the opening of the hole and thus regulate the flow of gas to be inhaled. U.S. Pat. No. 1,693,730, issued to Schroeder, on Dec. 4, 1928, discloses a device whereby the quantity of air inhaled corresponds to the depth of the users's breathing. There are no pins or piercing devices needed to dispense a predetermined amount of gas. The flow of the compressed gas creates a vacuum or partial vacuum which draws medicament into the device by droplets. These are then driven into the nozzle and eventually inhaled in a fine spray.

The prior art teaches a limited number of breath activated medication spray devices, but heretofore none are simple, cheap, disposable and reliable.

U.S. Pat. No. 3,636,949, issued to Kropp on Jan. 25, 1972, discloses a device whereby inhaling of a device causes a diaphragm to activate a complicated system of springs and levers, depressing the nozzle pin of an aerosol can, causing the aerosol to discharge into the user's mouth. This device attempts to accomplish a noble purpose, but fails. First, it does not function as intended. The same action that causes the diaphragm to activate the aerosol also opens a vent to allow air to enter the device, breaking the low pressure behind the diaphragm, robbing the diaphragm of its power. Secondly, the diaphragm must generate the considerable power necessary to depress the nozzle pin. (This is distinguished from the instant invention which uses a diaphragm only to generate the power necessary to slide a pin over a hole.) Third, the Kropp invention uses a complicated collection of levers and springs, which makes it big, heavy, expensive, and not cheap or disposable. Fourth, the Kropp device requires a lateral spray cap to come with its aerosol, and the standard medicinal aerosols on the market today do not have such a cap.

U.S. Pat. No. 3,812,854 issued to Michaels, et al on May 28, 1974, and U.S. Pat. No. 4,106,503 issued to Rosenthal and French on Aug. 15, 1978, both use ultrasonic nebulizers attached to respirators to allow medication to be inhaled. These devices are expensive, large electronic devices, are not cheap pocket sized and disposable, and make no use of the standard aerosol medicines on the market today.

U.S. Pat. No. 4,648,393, issued to Landis and Kassey on Mar. 10, 1987, is a "breath-activated medication spray" that attempts to address the timing and coordination problem. This device attempts to accomplish a noble purpose, but has several deficiencies. First, it is not necessarily inhalation activated. It must be manually cocked before it can work at all. When the batteries become weak or dead, its timing is first thrown off and then it stops functioning completely. In addition, this device can be inadvertently activated by jiggling or turning upside down. Secondly, it is a relatively large, heavy, and cumbersome device to use. Thirdly, the manufacture of the device is complicated and expensive and it cannot be made cheaply enough to be disposable, since it has two springs, batteries, a solenoid, an electrical timing switch, a moving magnet, and various electrical wirings. This device cannot be used by a person laying face up on his or her back. Furthermore, it is configured to spray, not directly into the inhalation nozzle, but onto the side wall of a breathing tube. As a result, this device encourages inaccurate dose dispensing since it is unpredictable how much of a dose will adhere to the side of the tube.

The present invention, on the other hand, is distinguishable from the prior art on many points. It is solely and reliably activated by the start of an inhalation. The present invention requires no manual cocking, and requires no batteries or power source. The present invention cannot be activated by jiggling. In its physical embodiment, the present invention is small, light, and simple to use. The present invention can be made out of molded plastic, with only one moving part. As a result, the present invention is cheap and can be used as a disposable dispenser. The present invention can be used in any orientation to the direction of gravity or in a weightless state. The present invention can be used on a patient in any position or while moving. The present invention can also be configured to spray directly out of its mouth nozzle without spray being forced onto the wall of the breathing cavity. It can be used in a mechanized respirator or an unconscious patient. It uses commonly available aerosol medicine spray cans, of measured dose or continuous spray.

It is an object of the present invention to provide an inhalation device that is truly activated by the inhalation of the user.

It is another object of the present invention to provide an inhalation device that is small, light, and simple to use.

It is still a further object of the present invention to provide an inhalation device that can administer a dosage of a medication at the very beginning of the inhalation.

It is still another object of the present invention to provide an inhalation device that can be used in any orientation.

It is still another object of the present invention to provide an inhalation device that minimizes the number of moving parts so as to be cheap to make and hence disposable.

It is an object of the present invention to be used in a mechanical respirator on an unconscious patient.

It is an object of this invention to use commonly available aerosol spray cans of medicine.

These and other objects and advantages of the present invention will become apparent from a reading of the attached specification and appended claims.

SUMMARY OF THE INVENTION

The present invention is an inhalation device for dispensing a medicament to a patient from a dispenser. The present invention comprises a body having an outwardly extending nozzle, a receptacle formed within the body for receiving the dispenser, and an activator positioned within the body that is mechanically interactive with the inhalation of a patient. The activator causes the dispenser to pass the medicament outwardly through the nozzle. The inhalation device also includes a vent that is formed in the body for carbureting air into the nozzle upon the inhalation by the patient. The present invention also includes a fixator that is detachably fastened to the body for affixing the dispenser in proper position within the receptacle.

The fixator comprises a vent formed in the body for allowing air to pass into the receptacle and out through the nozzle. This vent permits less than a free flow of air into the nozzle. The fixator is specifically a cap that is threadedly connectable to the body. This cap has an interior area that contains the dispenser. In general, the cap covers the receptacle of the body. The cap is threaded into a position in which the dispenser is in a dispensing mode within the receptacle.

The activator is responsive to a drop in air pressure within the nozzle. This activator causes the dispenser to release the medicament upon the reduction in air pressure within the nozzle. Specifically, the activator comprises a diaphragm positioned within the body. This diaphragm is deformable upon a reduction in air pressure within the nozzle. The activator also includes a pin that is fixedly positioned within the diaphragm and extends upwardly transverse to the plane of the diaphragm. This pin acts as a valve between the dispenser and the nozzle. The pin is attached to the diaphragm such that a deformation in the diaphragm causes a longitudinal movement in the pin. Specifically, this causes the pin to move longitudinally away from the dispenser. The diaphragm may form a portion of the outer surface of the body. This diaphragm flexes inwardly into the body upon a drop in air pressure within the nozzle.

The body comprises an atomizer positioned between the receptacle and the nozzle. This atomizer opens to the nozzle such that fluid is dispersed into the nozzle. The activator means acts as an air-responsive valve between the receptacle and the atomizer. Specifically, this air-responsive valve has a first position that prevents the passage of the medicament into the atomizer from the dispenser and a second position that allows the passage of such medicament into the atomizer.

The receptacle comprises a plurality of vanes formed in the receptacle. This plurality of vanes creates aerodynamic turbulence that assists in the atomizing of the medicament in the receptacle prior to the medicament reaching the atomizer.

A perforated plug is attached to the body adjacent the diaphragm. This perforated plug is arranged so as to shield the diaphragm from external contact.

The present invention may further include, in an alternative embodiment, a first tube that is connected to the body such that the vent communicates with the interior of the first tube. A second tube is connected to the nozzle of the body. The second tube allows for the transmission of aerosol medication to a location distal of the body. The present invention also may include a timer that is fastened to the body adjacent to the activator. This timer is for selectively restricting the activation of the activator. The timer specifically includes a clock mechanism for measuring time and for setting preset time intervals and an abutment member that is interactive with the clock mechanism. The abutment member is aligned with the pin on the diaphragm. This abutment member is selectively movable between a position abutting the pin and a position distal this pin. The movement of the abutment member is regulated by the clock mechanism. The diaphragm of the activator may also be modified so that it is deformable and moves the attached pin upon an increase in air pressure within the nozzle.

DETAILED DESCRIPTION OF THE INVENTION

Figure 1:
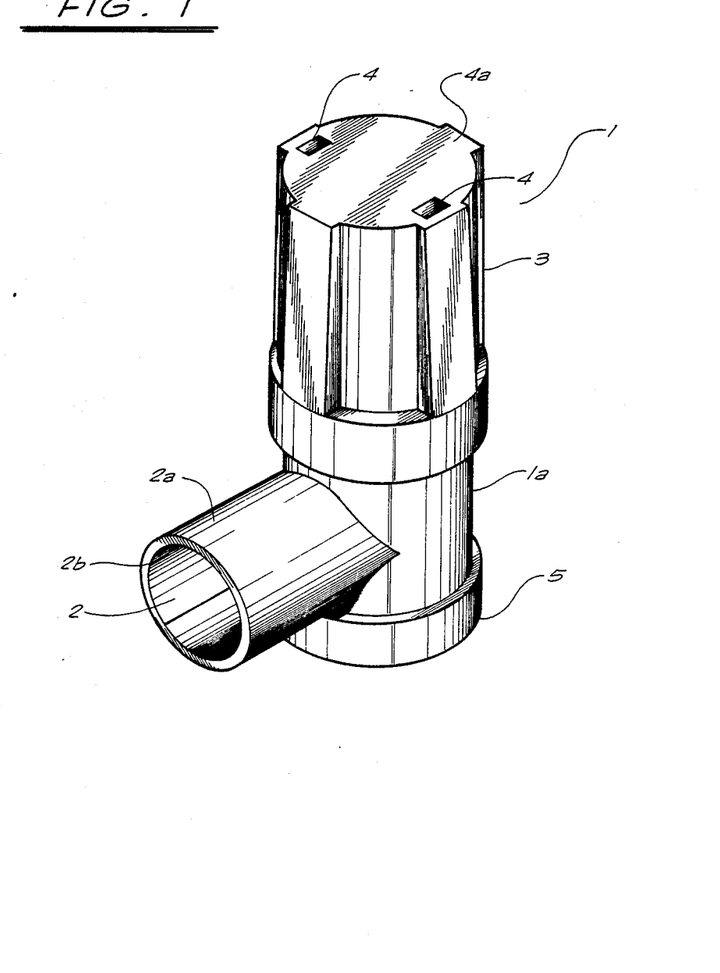
FIG. 1 is a perspective view of the exterior of the inhalation device of the present invention.

Referring to FIG. 1, there is shown a perspective view of the inhalation device 1 of the present invention. Specifically, inhalation device 1 is an automatic inhalation activated medication spray device. Inhalation device 1 comprises body 1a, nozzle 2, fixator 3, vents 4, and activator 5. The specifics of the interior configuration of the inhalation device is detailed in FIGS. 2, 5, and 6.

It can be seen that body 1a has a generally cylindrical configuration. Body 1a is a hand held mechanism of relatively small size. Body 1a may be manufactured of a metal or may be manufactured from a plastic. It is the intent of the present invention to provide a disposable inhalation device 1. Therefore, in the preferred embodiment of the present invention, the body 1a should be molded of a plastic material.

Nozzle 2 extends outwardly from body 1a. Nozzle 2 has an outer surface 2a that is integrally connected to the exterior of body 1a. The opening 2b of nozzle 2 communicates with the interior of body 1a. Nozzle 2 should have a suitable size for insertion into the mouth of the user. Ideally, the inhalation device 1 of the present invention will cause a fluid within a dispenser within fixator 3 to spray through body 1a to pass outwardly through nozzle 2 and into the mouth of the user.

Fixator 3 is threadedly connected to the top of body 1a. Fixator 3 serves to maintain the aerosol medication spray dispenser therewithin. As such, fixator 3 is a cap having a sufficient interior volume to contain the dispenser. In addition, fixator 3 will cover the open top of body 1a. When the fixator 3 is threaded into the position illustrated in FIG. 1, the dispenser contained therewithin (not shown) will be in a dispensing mode. Vents 4 are formed in the top surface 4a of fixator 3. Vents 4 allow air to pass into the interior of body 1a and outwardly through opening 2b of nozzle 2. Vents 4 should have quality sufficient to restrict the air flow into the interior of body 1a. Although a certain amount of air flow is restricted, it is necessary that air flow be achieved so as to provide for the proper carburetion effects of the present invention. Although the vents 4 are illustrated as located on the top surface 4a of fixator 3, it may be also possible to incorporate the vents 4 elsewhere on the body 1a or into the threaded portion between the body 1a and the fixature 3. The illustration of FIG. 1 is for the purpose of illustrating the need for the vents, rather than a specific requirement of the present invention.

Figure 5:
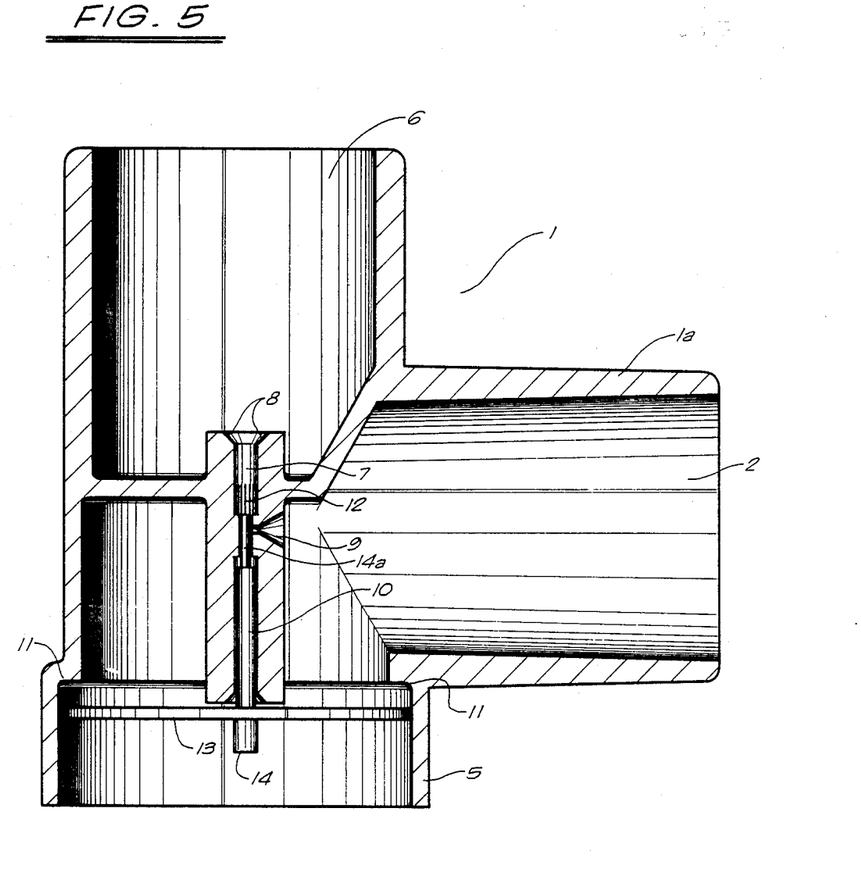
FIG. 5 is a cross-sectional view, in side elevation, showing the configuration of the inhalation device of the present invention prior to inhalation.

It can be seen that the activator 5 is affixed to the bottom portion of body 1a of inhalation device 1. The specifics of the activator 5 are not illustrated in FIG. 1. FIG. 5 shows that the mechanism is attached to the bottom of the body 1a. Additionally, as described in an alternative embodiment of the present invention, the ring 5 may also be a timer mechanism that can be incorporated so as to prevent continuous usage of the inhalation device 1.

Figure 2:
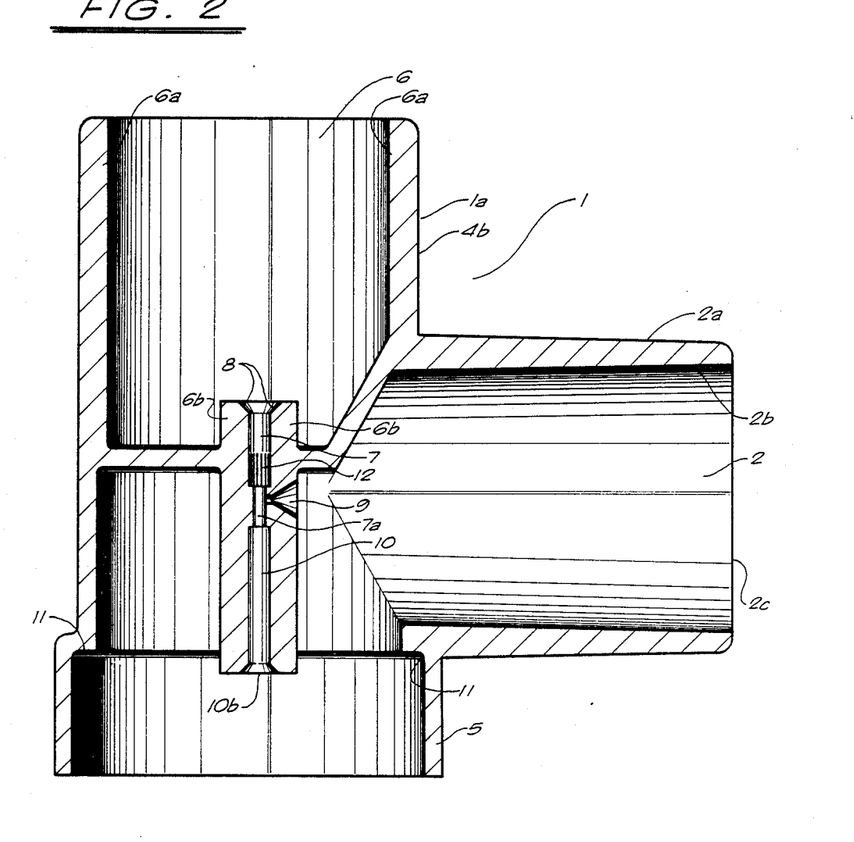
FIG. 2 is a cross-sectional view, in side elevation, of the body of the present invention.

FIG. 2 is a cross-sectional view of the body 1a of inhalation device 1. Initially, it can be seen that the nozzle 2 extends outwardly from the cylindrical surface 4b of body 1a. Nozzle 2 includes the cylindrical walls 2a which encompass the opening 2b. As such, aerosol sprayed fluids will be dispersed through nozzle 2 and outwardly through the end 2c of nozzle 2.

FIG. 2 also shows the receptacle 6 for the receipt of the aerosol dispenser therein. Receptacle 6 has a roughly cylindrical configuration that will conform to the size of the aerosol dispenser. The forward area 7 of the receptacle 6 is a molded area that is formed specifically for the receipt of the nozzle of the dispenser. Specifically, walls 6a extend downwardly and somewhat inwardly so as to join nozzle receptacle walls 6b. Bevelled edges 8 of walls 6b receive and depress the nozzle of the aerosol dispenser. Forward area 7 is a rather tubular area that generally matches the nozzle of the aerosol dispenser. An atomizer outlet 9 is formed in walls 6b so as to allow the fluid to be dispersed, in atomized fashion from interior area 7a outwardly through atomizer 9 and into the area of nozzle 2. A slideway 10 for the pin of the activator (to be described hereinafter) is formed within walls 6b. This is a tubular pathway of rather smooth configuration that allows an easy passage of a pin therein. Opening 10a is formed on the lower portion of wall 6b so as to allow the activator pin easy entry into slideway 10.

Shoulders 11 are formed as inner indentations within the body 1a. The shoulders 11 are formed of the interior of body 1a so as to abut the edges of the diaphragm (to be described hereinafter).

A plurality of turbulence ribs (or vanes) 12 are formed within the forward area 7 of the receptacle 6. In use, these vanes create turbulence to assist in the atomization of the sprayed medicament prior to reaching atomizer 9.

Figure 3:
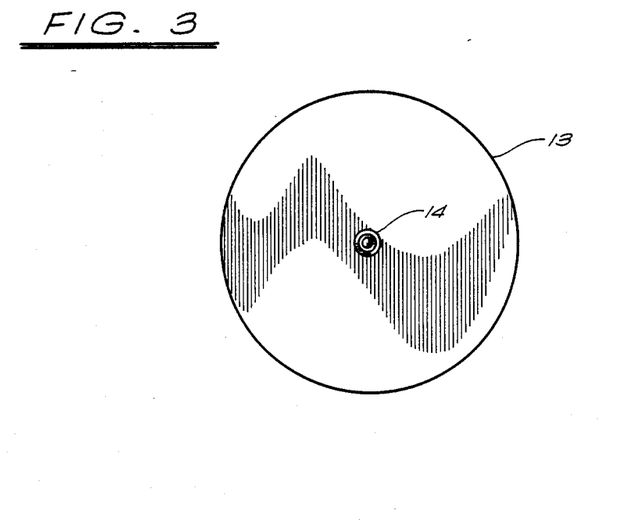
FIG. 3 is a frontal view showing the activator/diaphragm of the present invention.

FIG. 3 is a frontal view of the activator/diaphragm 13. Activator/diaphragm 13 is an elastic member of circular configuration. Activator/diaphragm 13 should have an elasticity suitable for permitting deformation in the presence of an inhalation by the user of the inhalation device 1. The circularity of activator diaphragm 13 is of a sufficient size to fit within the area defined beneath the shoulders 11 of the body 1a. Pin 14 is fixed to the middle of diaphragm 13. Pin 14 is of a type suitable for insertion into the opening 10b and into the slideway 10 of the receptacle walls 6b.

Figure 4:
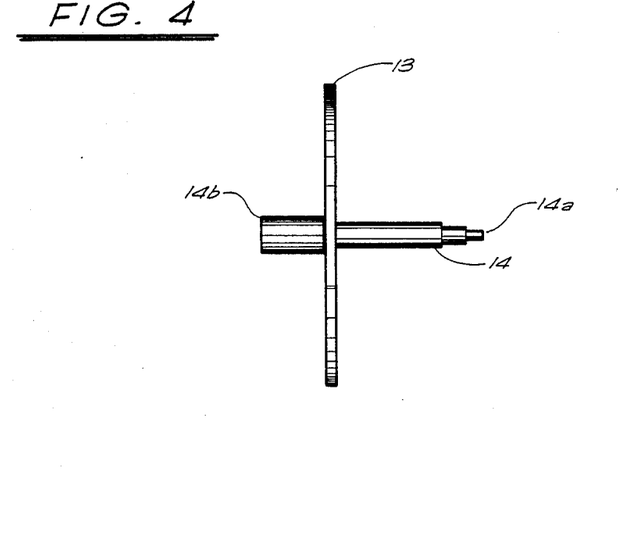
FIG. 4 is a side view showing the activator/diaphragm of the present invention.

FIG. 4 is a side view of the activator diaphragm of FIG. 3. Specifically, it can be seen that the diaphragm 13 has a relatively narrow configuration. The pin 14 is fastened to and extends through the diaphragm 13. Pin 14 generally narrows at its end 14a so as to accommodate its positioning within sideway 10. Pin 14 extends through diaphragm 13 to end 14b. End 14b will be located beneath the diaphragm in its assembled configuration in the inhalation device 1. End 14b may act as an abutment surface when the present invention is utilized in conjunction with a timing device (to be described hereinafter).

FIG. 5 is similar to FIG. 2, except that it shows the diaphragm 13 and the activator pin 14 as utilized within the inhalation device 1. The configuration, illustrated in FIG. 5, is the configuration of the present invention in the absence of an inhalation. As can be seen in FIG. 5, the diaphragm 13 is not deformed. The walls of diaphragm 13 extend straight outwardly and generally near the abutment surface of shoulders 11. It can be seen that the pin 14 extends upwardly through slideway 10. The upper portion 14a of pin 14 extends through the slideway 10 and is in interference relationship with the atomizer opening 9. As such, the configuration illustrated in FIG. 5 acts as a block to the passage of fluid, or gas, into and through nozzle 9. For the purposes of illustration, until upper portion 14a of pin 14 is moved away from the opening of the atomizer 9, no gas, or fluid, can pass outwardly to the user.

Figure 6:
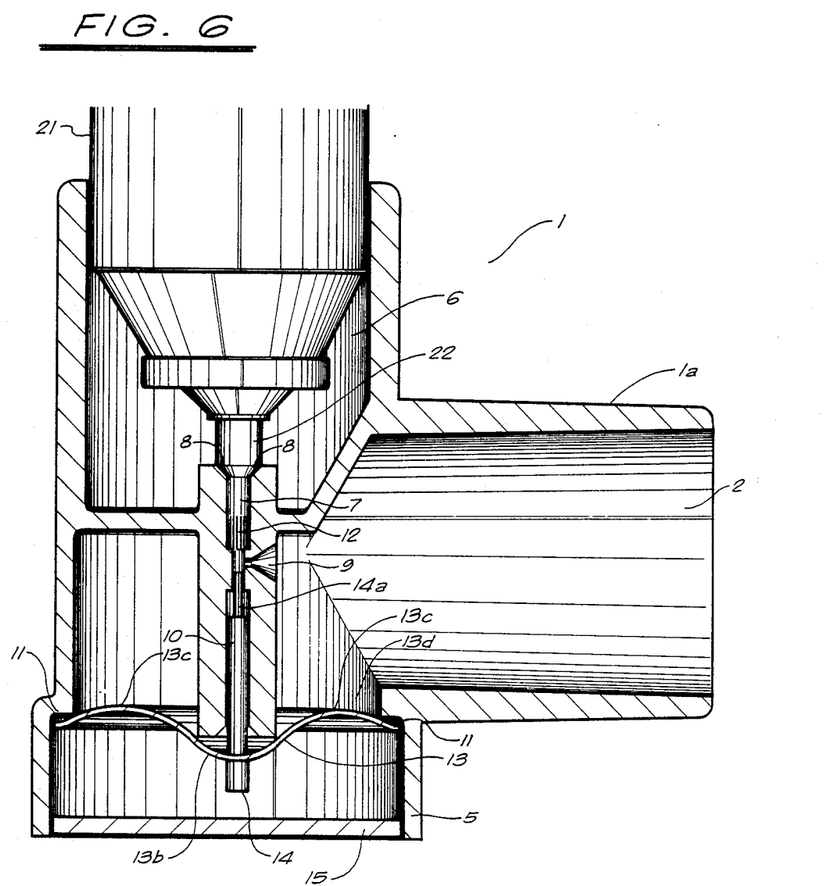
FIG. 6 is a cross-sectional view, in side elevation, of the inhalation device of the present invention during inhalation.

FIG. 6 is similar to FIG. 5, except that it shows the diaphragm 13 as flexed in response to reduced pressure within nozzle 2. It can be seen that the specific flexure of the diaphragm 13 causes the walls 13c of diaphragm 13 to flex upwardly into the opening 13d within body 1a. In other words, the suction in nozzle 2 forces these portions 13c of the diaphragm 13 upwardly. Such deformation of these portions 13c of diaphragm 13 work to cause the lower portion 13b of diaphragm 13 to move downwardly. As a result, pin 14 is also drawn downwardly. The upper portion 14a of pin 14 slides downwardly and serves to open atomizer 9. It can also be seen that the diaphragm 13 is now in abutment with the shoulders 11 of body 1a. Such abutment assists in the deformation of the diaphragm 13 and results in the action described hereinbefore.

Spray enters nozzle 2 from the aerosol dispenser 21. Aerosol dispenser 21 is a type of dispenser that can be commonly purchased for use by asthmatics. Aerosol dispenser 21 is placed into the receptacle 6 of the inhalation device 1 of the present invention. As described in conjunction with FIG. 1, the cap (or fixator) 3 is placed over the aerosol dispenser 21 so as to draw aerosol dispenser 21 downwardly into receptacle 6. The aerosol nozzle 22 of aerosol dispenser 21 goes into, abutment with the bevelled edges 8 of forward area 7. When this abutment occurs and when the fixator 3 causes the nozzle 22 to become compressed, the aerosol is dispensed from the dispenser 21 and into the forward area 7 of receptacle 6.

When the diaphragm is in the condition, illustrated in FIG. 5, the forward portion 14a of pin 14 causes a blockage of the atomizer 9. As such, when gas is dispensed from dispenser 21, such gas will reside in the forward area 7 of the receptacle 6. Upon an inhalation the pin 14 will move, as illustrated in FIG. 6, with the deformation of the diaphragm 13. This causes the pin 14 to move beyond the atomizer 9 and, thus, allows the gas to be expelled, in atomizer fashion, through atomizer nozzle 9. When such atomizing occurs, the aerosol medication, along with carbureted air, is received by the user through nozzle 2.

A perforated plug 15 is shown as installed at the bottom of activator 5. This perforated plug 15 prevents external contact with diaphragm 13 and prevents the diaphragm from separating from the body 1a.

As illustrated in FIGS. 1–6, the present invention acts as an automatic inhalation activated medication spray device that, by sucking on the nozzle 2, activates the aerosol pressurized medication canister for the purpose of delivering a dose of its contents to the lungs of the user. The present invention allows asthmatics to treat themselves with a disposable device that ideally times the spray for the beginning of the inhaled breath. It can be seen that this device has only one moving part, the diaphragm/pin assembly 13. This device has no batteries, excessive moving parts, or power requirements.

The present invention carburetes atmospheric air with the medication spray so as to permit a full breath through the device to the user. The amount of air carbureted with the dispensing of the medication is a matter of design choice. The only restriction to the requirement for venting is that less than a free flow of air be transmitted by the vents to the user.

The aerosol canister 21 is a measured dose canister. This is of a standard configuration and is manufactured by a wide variety of pharmaceutical companies. In contrast to standard aerosols, a continuous spray is not dispensed. Rather, a short spray results from releasing a fixed dose of medicine. The dispenser 21 will not dispense again until the nozzle pin is released and depressed again. By atomizing, and dispensing into nozzle 2 at the beginning of a breath, all of the medicine is carried to the lungs at the beginning of the inhalation, rather than dispersed in the mouth, throat, or spray device. As such, a proper dose of medication is actually received by the patient. There is no need to have a "make-up" dose. Furthermore, the present invention prevents overdosage or improper administration. The aerosol canister 21 may also be a continuous spray canister.

Since asthmatics may have coordination problems, especially during attack, the present invention solves that problem by allowing the dosage to be dispensed by mere inhalation. There is no need for manual manipulation nor need for accurate dispensing. In addition, there is no difficulty in timing the breath spray so that the spray is received during the beginning of the inhalation. As such, the present invention achieves a number of advantages that are not found in the prior art dispensing devices.

Figure 7:
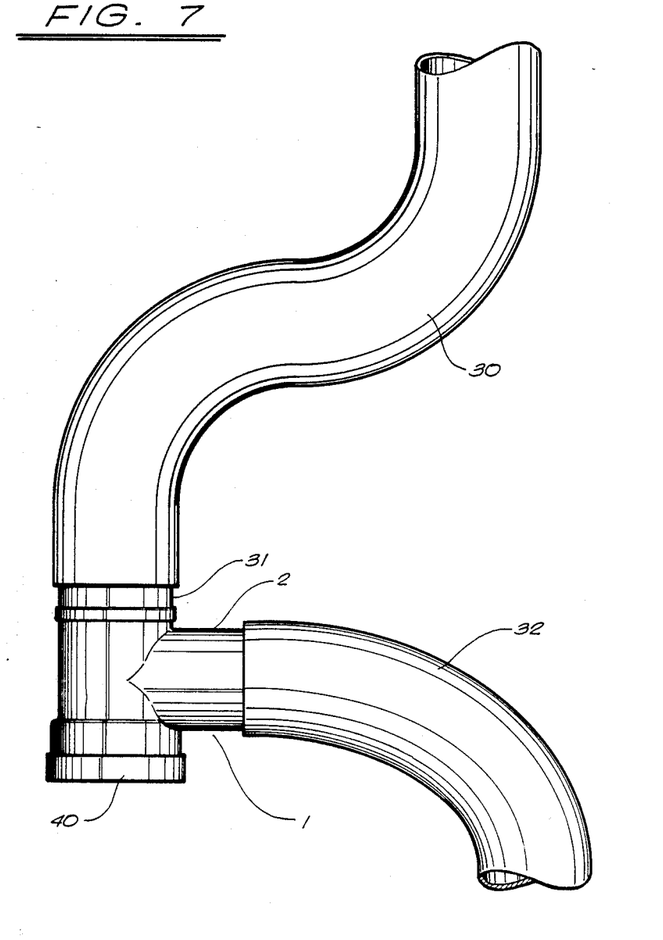
FIG. 7 is a diagrammatic illustration showing an alternative embodiment of the inhalation device of the present invention.
Figure 8:
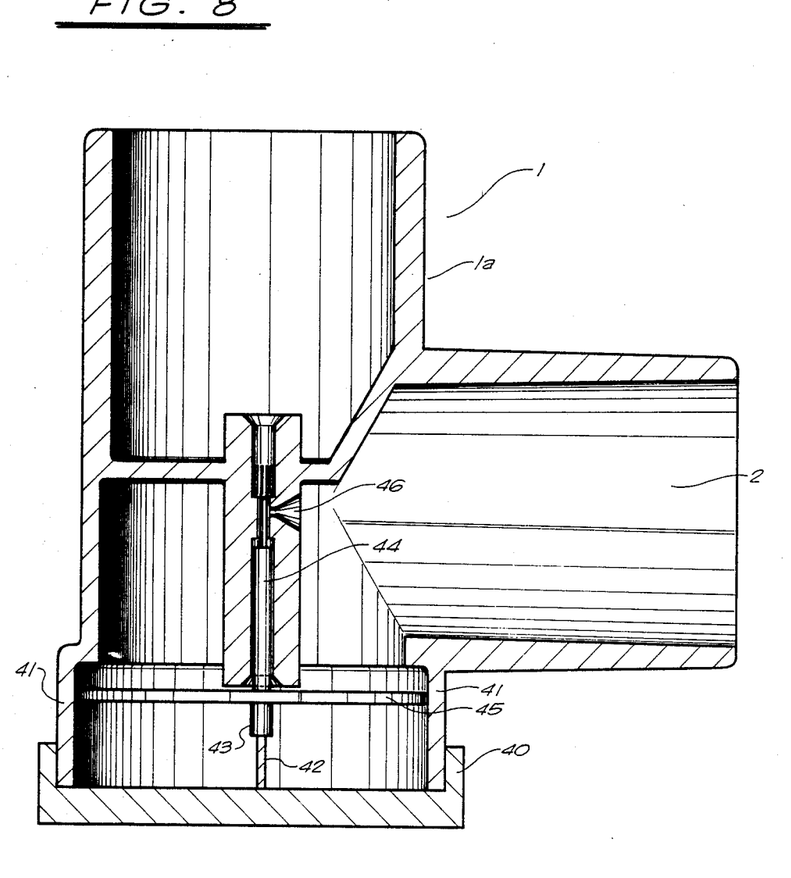
FIG. 8 is a cross-sectional view, in side elevation, showing an alternative embodiment of the present invention utilizing a timer mechanism in conjunction with the activator mechanism of the present invention.

An alternative embodiment of the present invention is illustrated in FIG. 7. Specifically, FIG. 7 is a schematic illustration showing the arrangement of the inhalator device 1 as connected to a respirator and transmitted to a patient. It can be seen in FIG. 7 that first tube 30 is a tube that extends to a respirator. This respirator is fastened to the receptacle 31 of inhalation device 1. Air from respirator 30 is properly vented to the patient at the end of the second tube 32 by way of the vents in the receptacle 31. The second tube 32 delivers air and medication directly to the patient by virtue of the interaction with the inhalation device 1. When a burst of oxygen is transmitted through first tube 30, this creates a pressure increase in the nozzle 2 of inhalation device 1. When this pressure increase occurs, the medication is dispensed outwardly to tube 32. Medication is then transported directly to the patient's lungs by this configuration. As a result, this alternative embodiment allows for the dispensing of medication by way of the forced pressure through the venting of the receptacle 31. It can be seen that medication dispensing occurs when a pressure increase occurs through the venting area 31. If necessary the diaphragm can be modified to flexably respond to pressure increases in the nozzle instead of, or in addition, to pressure decreases.

Since the embodiment of FIG. 7 dispenses medication quite frequently, it is important that the device of FIG. 7 have a timing apparatus 40 attached to the inhalation device 1. As a result, the timing apparatus 40 will only permit the dispensing of the aerosol medication at properly preset time intervals.

FIG. 8 shows the arrangement of the timing apparatus 40 as utilized in conjunction with the body 1*a*. It can be seen that timing apparatus 40 is fitted to the exterior surface 41 of body 1*a*. Such attachment can be accomplished by threading, gluing, or other sealing techniques. Timing device 40 includes an internal clock (not shown) and an abutment member 42. The clock contained within timing mechanism 40 is of conventional configuration. What is important with the use of the timing mechanism 40 is that the clock within the mechanism be interactive with the abutment member 42. This configuration can be in the nature of a solenoid arrangement, or other mechanical configuration. In essence, during periods of non-dispensing, the abutment member 42 will abut the end 43 of pin 44. This present abutment arrangement will prevent movement of the pin despite any deformation of diaphragm 45. As such, pin 44 will serve to block any medication from passing into atomizer 46. Until the abutment member 42 is removed from the end 43 of pin 44, no medication is dispensed.

When the present interval occurs, the abutment member 42 will be drawn into timing mechanism 40. In other words, the abutment member 42 is retracted. Once the abutment member 42 is retracted, the diaphragm 45 is free to deform as needed. When deformation occurs, the pin 44 is drawn downwardly thereby freeing the atomizer for the dispensing of medication into nozzle 2.

As stated previously, the timing mechanism 40 is particularly important when dispensing medication to a patient on a respirator. The timing mechanism 40 may also be useful when dispensing medication to other patients who have the ability to utilize the inhalation device 1 on their own. The dispensing of medication may only be necessary during certain time periods. As such, the timing mechanism 40 can be utilized so as to prevent the patient from getting an overdose. Since the timing mechanism 40 may be more expensive than the inhalation device 1, it may be most expedient to cause the timing mechanism 40 to threadedly engage the walls 41 of body 1*a*. As such, the timing mechanism 40 may be interchangeable between various inhalation devices 1.

The inhalation device 1 may be utilized in conjunction with breathing tubes, of the type illustrated in FIG. 7, in a variety of ways. One example is that the inhalator device 1 may be installed in the tubes such that the nozzle of the inhalation device fits into one leg of a Y-joint in the tube. In this manner, the air forced through the tube will inhale fresh atmospheric air through the inhalation device 1 so as to carry medication into the tube. The inhalation device may also be installed in line in the tube such that the air that is forced through the respirator enters through the vents of the inhalation device and outwardly through the nozzle of the inhalation device. When the air that is forced into the patient increases the pressure across the interface of the diaphragm, this causes the dispenser to dispense the medicator directly into the patient.

The present invention, in its plurality of embodiments, accomplishes the purposes of delivering the aerosol medication to the patient at the beginning of the inhalation cycle. Additionally, the inhalation device of the present invention can be simply manufactured, simply used, and easily disposed of. As a result, there is little need for additional sterilization, or other manipulative procedures required for the reuse of the present invention. Since the aerosol medications are readily available, the present invention is easily adapted to presently available medications. As such, the present invention achieves a number of advantages that are not found in the prior art.

The foregoing disclosure and description of the invention is illustrative and explanatory thereof, and various changes in the method steps, as well as in the details on the illustrated apparatus, may be made within the scope of the appended claims without departing from the true spirit of the invention. The present invention should be limited only by the following claims and their legal equivalents.

We claim:

1. An inhalation device for dispensing a medicament to a patient from a dispenser comprising:

a body having an outwardly extending nozzle;

a receptacle formed within said body for receiving said dispenser;

an activator means positioned within said body, said activator means being mechanically interactive with the inhalation of said patient, said activator means for causing said dispenser to pass said medicament outwardly through said nozzle, said activator means being responsive to a change in air pressure within said nozzle, said activator means causing said dispenser to release said medicament upon the reduction in air pressure, said activator means comprising a diaphragm within said body, said diaphragm being deformable upon a reduction in air pressure within said nozzle; and a vent formed in said body for carbureting air into said nozzle upon the inhalation by said patient.

2. The device of claim 1, further comprising:

fixator means detachably fastened to said body, said fixator means for affixing said dispenser in position within said receptacle.

3. The device of claim 1, said activator means further comprising:

a pin fixedly positioned within said diaphragm and extending into the device transverse to the plane of said diaphragm, said pin acting as a valve between said dispenser and said nozzle.

4. The device of claim 3, said pin attached to said diaphragm such that a deformation of said diaphragm causes longitudinal movement of said pin.

5. The device of claim 4, said pin connected to said diaphragm such that a deformation of said diaphragm causes said pin to move longitudinally away from said dispenser.

6. The device of claim 1, said diaphragm forming a portion of the outer surface of said body, said diaphragm flexing upon a change in air pressure within said nozzle.

7. The device of claim 1, said body comprising:

an atomizer positioned between said receptacle and said nozzle, said atomizer opening to said nozzle such that atomized fluid is sprayed into said nozzle.

8. The device of claim 1, said diaphragm comprised of an elastic material.

9. The device of claim 1, said body further comprising:

a perforated plug attached to said body adjacent said diaphragm, said perforated plug arranged so as to shield said diaphragm from external contact.

10. An inhalation device for dispensing a medicament to a patient from a dispenser comprising:

a body having an outwardly extending nozzle;

a receptacle formed within said body for receiving said dispenser;

an activator means positioned within said body, said activator means being mechanically interactive with the inhalation of said patient, said activator means for causing said dispenser to pass said medicament outwardly through said nozzle, said activator means being responsive to a change in air pressure within said nozzle, said activator means causing said dispenser to release said medicament upon the reduction in air pressure, said activator means comprising a diaphragm within said body, said diaphragm being defomable upon a reduction in air pressure within said nozzle;

fixator means detachably fastened to said body, said fixator means for affixing said dispenser in position within said receptacle; and a vent formed in said fixator means for allowing air to pass into said receptacle and through said nozzle, said vent permitting less than a free flow of air into said receptacle.

11. The device of claim 6, said fixator means comprising:

a cap threadedly connected to said body, said cap having an interior area for containing said dispenser, said cap covering said receptacle of said body.

12. The device of claim 11, said cap being threaded into a position in which said dispenser is in a dispensing mode within said receptacle.

13. An inhalation device for dispensing a medicament to a patient from a dispenser comprising:

a body having an outwardly extending nozzle;

a receptacle formed within said body for receiving said dispenser, said body comprising an atomizer positioned between said receptacle and said nozzle, said atomizer opening to said nozzle such that atomized fluid is sprayed into said nozzle;

an activator means positioned within said body, said activator means being mechanically interactive with the inhalation of said patient, said activator means for causing said dispenser to pass said medicament outwardly through said nozzle, said activator means being an air-responsive valve between said receptacle and said atomizer, said air-responsive valve having a first position preventing the passage of said medicament into said atomizer from said dispenser and a second position allowing the passage of said medicament into said atomizer.

14. The device of claim 13, said receptacle comprising:

a plurality of vanes formed in said receptacle, said plurality of vanes causing turbulence to assist in the atomization of said medicament in the receptacle prior to reaching said atomizer.

15. An inhalation device comprising:

a body;

a receptacle formed in said body, said receptacle for receiving an aerosol medication dispenser;

vent means formed in said body so as to pass air under pressure into said body;

a nozzle formed in said body for passing air from aid vent means outwardly from said body; and activation means attached within said body for activating said dispenser upon the passing of air through said vent means, said activation means causing said dispenser to dispense aerosol medication; said activation means comprising:

a flexible diaphragm positioned within said body, said diaphragm being deformable upon an increase of air pressure within said nozzle; and a pin fixedly positioned to said diaphragm and extending into the device transverse to the plane of said diaphragm, said pin acting as a valve between said dispenser and said nozzle.

16. The device of claim 15, further comprising:

a first tube connected to said body such that said vent means communicates with the interior of said tube; and a second tube connected to said nozzle, said second tube for transmitting said aerosol medication to a location distal of said body.

17. The device of claim 15, further comprising:

timer means fastened to said body adjacent said activation means, said timer means for selectively restricting the activation of said activation means.

18. The device of claim 17, said timer means comprising:

a clock mechanism for measuring time and for setting pre-set time intervals; and an abutment member interactive with said clock mechanism said abutment member aligned with said pin on said diaphragm, said abutment member selectively movable between a position abutting said pin and a position distal said pin, the movement of said abutment member being regulated by said clock mechanism.

19. The device of claim 16, further comprising:

said first tube connected, at its end opposite from the end connected to said vent means, to a mechanical respirator, and said second tube connected, at its end opposite from the end connected to said nozzle, to the lungs of a patient.

20. A method of dispensing an aerosol medication to a patient comprising the steps of:

inserting an aerosol medication dispenser into a body such that said aerosol medication dispenser is compressed within said body, said body having a desired air pressure therewithin, said step of inserting comprising:

placing said aerosol medication dispenser into said body such that said aerosol medication dispenser abuts a surface in said body;

positioning a cap over said aerosol medication dispenser; and tightening said cap to said body such that said cap causes said aerosol medication dispenser to become compressed within said body;

inhaling on a nozzle of said body such that a reduction in air pressure occurs within said body; and deforming a diaphragm within said body such that said diaphragm causes a valve pin to activate said aerosol medication dispenser so as to cause said aerosol medication to pass from said dispenser into said nozzle.

21. A method of dispensing an aerosol medication to a patient comprising the steps of:

inserting an aerosol medication dispenser into a body such that said aerosol medication dispenser is compressed within said body, said body having a desired air pressure therewithin;

inhaling on a nozzle of said body such that a reduction in air pressure occurs within said body, said step of inhaling comprising the step of:

venting air into said body during the inhaling on the nozzle of said body, said venting being less than a free flow air into said body; and deforming a diaphragm within said body such that said diaphragm causes a valve pin to actuate said aerosol medication dispenser so as to cause said aerosol medication to pass from said dispenser into said nozzle.

* * * * *